United States Patent [19]

Hahn et al.

[11] Patent Number: 4,838,246

[45] Date of Patent: Jun. 13, 1989

[54] APPLICATION PART FOR AN ENDOSCOPE

[75] Inventors: Andreas Hahn, Sauerlach; Fritz Wondrazek, Pfaffenhofen; Frank Frank, Ebersberg, all of Fed. Rep. of Germany

[73] Assignee: Messerschmitt-Bölkow-Blohm GmbH, Munich, Fed. Rep. of Germany

[21] Appl. No.: 85,396

[22] Filed: Aug. 13, 1987

[30] Foreign Application Priority Data

Aug. 13, 1986 [DE] Fed. Rep. of Germany ....... 3627522

[51] Int. Cl.⁴ .............................................. A61B 1/06
[52] U.S. Cl. .................................... 128/6; 128/303.15
[58] Field of Search ............... 128/4, 6, 303.1, 303.15

[56] References Cited

U.S. PATENT DOCUMENTS

| 2,559,227 | 7/1951 | Reiber | 128/24 A |
|---|---|---|---|
| 4,146,019 | 3/1979 | Bass et al. | 128/6 |
| 4,281,646 | 8/1981 | Kinoshita | 128/6 |
| 4,419,987 | 12/1983 | Ogw | 128/6 X |
| 4,608,979 | 9/1986 | Breidenthal et al. | 128/303.1 |
| 4,732,448 | 3/1988 | Goldenberg | 128/6 X |

FOREIGN PATENT DOCUMENTS 2538960 7/1977 Fed. Rep. of Germany .
2945080 4/1986 Fed. Rep. of Germany .
3506249 8/1986 Fed. Rep. of Germany .

OTHER PUBLICATIONS

Fair, "In vitro destruction of urinary calculi by laser-induced stress waves" Medical Instrumentation, vol. 12, No. 2, Mar.-Apr. 1978.

Primary Examiner—William H. Grieb
Attorney, Agent, or Firm—Kenyon & Kenyon

[57] ABSTRACT

The disclosure relates to an application part for rigid or flexible endoscopes having a viewing channel and a working channel extending parallel to the viewing channel, with the working channel being equipped with a guide as well as a defined stop for a fiber optic waveguide, which can be inserted and coupled with a laser light source, and the working channel having optics for concentrating the laser light emerging from the fiber optic waveguide onto a punctiform area. The part of the working channel surrounding the punctiform area is formed as shock wave reflector. Further, a flushing channel is provided, the outlet opening of which is at least partially directed onto the face of the optics from which the light emerges.

15 Claims, 1 Drawing Sheet

APPLICATION PART FOR AN ENDOSCOPE

BACKGROUND AND SUMMARY OF THE INVENTION

The invention relates to an application part for use in either rigid or flexible endoscopes and having a viewing channel, and a working channel extending parallel to the viewing channel. The working channel is equipped with a guide as well as a defined stop for an insertable fiber optics waveguide which can be coupled to a laser light source.

A device of this nature is known, for example, from DEP No. 29 45 080. This device is used for endoscopic laser irradiation of urinary bladder tumors with the laser light emerging from the light waveguide being directed directly onto the tissue to be irradiated. The object of the present invention is to provide an application part for rigid or flexible endoscopes, with which fragmentation of concrements, such as bladder, urinary bladder, kidney or gall stones within living bodies, becomes possible.

The objective of the invention is achieved through an application part for flexible or rigid endoscopes wherein the working channel has an optics arrangement for concentrating the laser light emerging from the fiber optic wave guide onto a punctiform region and, further, the working channel extends beyond the optics arrangement toward the punctiform region to form a shock wave reflector. Moreover, a flushing channel is provided having an outlet opening which is at least partially directed toward the face of the optics arrangement.

A device for fragmenting a solid body is described in the earlier application No. P 35 06 249.5. This device, however, does not serve as an application part for a rigid or flexible endoscope.

The application part according to the invention can, for example, be either integrated into a rigid endoscope or placed onto a flexible endoscope. With an endoscope equipped in this way, bladder, urinary, kidney or gall bladder stones can be directly fragmented into extremely small fragments with shock waves, without the shock waves having to pass through the body, and with the stones under observation continuously throughout the procedure. The fragments can then be flushed out without problems or they can be passed naturally.

Below the invention is described in greater detail in conjunction with an embodiment represented schematically in the figures, in which

DETAILED DESCRIPTION

Figure 1:
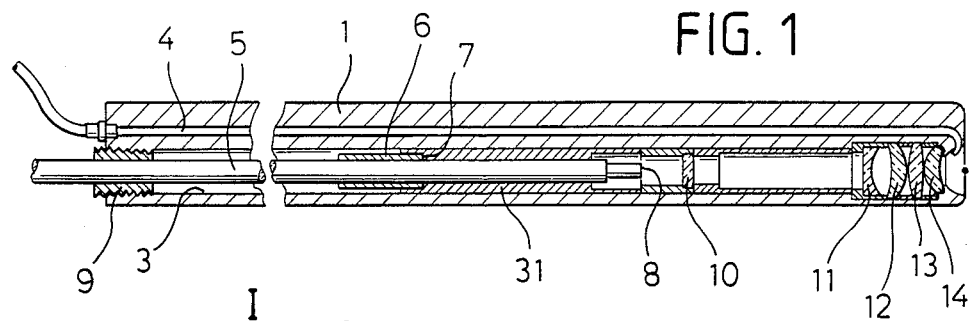
FIG. 1 is a longitudinal section along line I—I of FIG. 2 through the working channel of an application part for a rigid or flexible endoscope.

The application part shown in FIG. 1 consists essentially of a cylindrical part 1 with three channels extending parallel, of which one is a viewing channel 2, another a working channel 3, and the last a flushing channel 4. The working channel 3 has a guide 31 for a fiber optic waveguide 5, onto which a stop ring 6 is clamped or fastened with adhesive agents. The fiber optic waveguide 5 is slid into the working channel 3 until the stop ring 6 rests against a specially formed part 7 of the guide 31. In this manner, the position of the end face 8 of the fiber optic waveguide 5 within the working channel 3 is precisely defined. To prevent the sliding of the fiber optic waveguide 5 within the working channel 3, the latter is equipped with a clamping device 9.

The fiber optic waveguide 5 is connected at the inlet side with a laser light source known per se and therefore not illustrated. The laser light emerging from the end face 8 of the fiber optic waveguide 5 is bundled by an optics arrangement including lenses 10 to 14 onto a punctiform area 15. For this purpose, the optics arrangement is formed as a reduction optics arrangement with a reproduction ratio of 1:4 to 1:10, which reproduces the end face 8 in the region 15 correspondingly reduced.

The light intensity coupled into the waveguide 5 as well as the reproduction ratio of the optics are so adapted to each other that in the region 15 a so-called "breakdown-effect" occurs, as described in the above mentioned German patent application No. P 35 06 249.5 or in the dissertation by Dipl.-Phys. Jurgen Munschau "Theoretische und experimentelle Untersuchungen zur Erzeugung, Ausbreitung and Anwendung laserinduzierter StoBwellen" ("Theoretical and experimental investigation concerning generation, diffusion and application of laser-induced shock waves."), TU Berlin, Berlin 1981. The shock wave generated by this "breakdown-effect" is focused by a spherical or elliptical shock wave reflector 16. When using a spherical reflector it is positioned such that the focus coincides with the focal point of the optics in region 15. When using an elliptical shock wave reflector with two focal points, one focal point coincides with the focal point of the optics in region 15, while the other focal point is directed onto the surface of the concrement to be fragmented. The illustrated embodiment has a spherical shock wave reflector and the area 15 lies on the plane defined by the outer border 17 of the shock wave reflector 16 in such a way that the endoscope can be placed directly onto the concrement to be fragmented. Thus, in each instance only fragments of the outer layer of the concrement are removed. This ensures that only extremely small fragments are generated, which can either be flushed out or passed by natural means.

Since the generated shock waves exert great stress on the optics, in particular on the lens 14, at least this lens 14 and, because of the high light intensities, possibly also the field lens 10 are made from quartz glass or sapphire. When shaping the lens 14 it is best if here a concave-convex lens is employed, with the curvature of the concave face corresponding approximately to that of the shock wave reflector 16. In this way, the lens 14 partially assumes the function of a shock wave reflector. Further, the lens 14 must be sealed gas and liquid-tight as well as shock-proof against the shock wave reflector 16 and the sealing material 18 must be made from a particularly elastic material. Silicon is an especially well suited material for this purpose.

Figure 3:
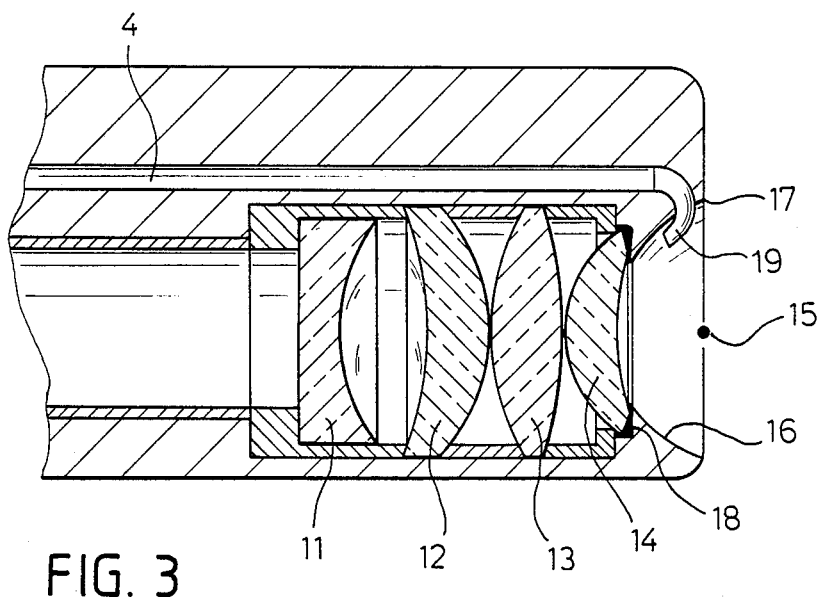
FIG. 3 is an enlarged view of the distal end of the application part of FIG. 1.

Since during treatment the front lens 14 must be kept clean, the flushing channel 4 has at its distal end a bent nozzle 19, which directs a jet of flushing fluid directly onto the lens 14 (see FIG. 3).

Figure 2:
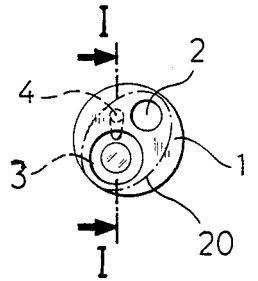
FIG. 2 represents a view from above onto the distal end of a device according to FIG. 1.

With the currently available fiber optic waveguides and optics working channel diameters of 2 to 3 mm, the entire diameter of the application part, which is circular in cross section, is approximately 5 to 7 mm. The cross sectional area can be correspondingly reduced if the outer contour is even further adapted to the envelope 20 of channels 2, 3, and 4 (see FIG. 2).

What is claimed is:

1. In an application part for an endoscope, said application part comprising a viewing channel and a working channel extending parallel to said viewing channel; said working channel including a guiding means and a defined stop for slidable insertion of a fiber optic waveguide, selectively coupled to a laser light source, an improvement in said application part wherein said working channel includes an optics arrangement for concentrating the laser light emerging from the fiber optic wave guide onto a punctiform region, and further said working channel being arranged to extend beyond the optics arrangement in the direction of said punctiform region to form a shock wave reflector and further comprising a flushing channel having an outlet opening which is at least partially directed toward the face of said optics arrangement from which the light emerges.

2. The application part of claim 1, wherein said optics arrangement on the side facing the shock wave reflector includes a concave-convex lens, the concave surface of which is connected at the outer edge with said shock wave reflector.

3. The application part of either claims 1 or 2, wherein at least one lens of the optics arrangement adjacent to said shock reflector includes an elastic seal in the region of the lens mount.

4. The application part of any one of claims 1 or 2, wherein the lenses of said optics arrangement facing the shock wave reflector and the fiber optic waveguide being made from quartz glass.

5. The application part of any one of claims 1 or 2, wherein the lenses of said optics arrangement facing the shock wave reflector and the fiber optic waveguide being made from sapphire.

6. The application part of any one of claims 1 or 2, wherein the optics arrangement is a reduction optics arrangement with a reproduction ratio of no more than 1:4.

7. The application part of any one of claims 1 or 2, wherein the focal point of the optics arrangement and the focus of the shock wave reflector lie on the plane defined by the distal edge of the shock wave reflector.

8. The application part of any one of claims 1 or 2, wherein the viewing, working, and flushing channels extend parallel to one another and have a common sheathing.

9. The application part of claim 8 wherein said common sheathing is of a circular cross section.

10. The application part of claim 8 wherein said common sheathing is of an elliptical cross section.

11. The application part of claim 8 wherein said common sheathing is of an oval cross section.

12. The application part of claim 8 wherein said common sheathing is of a non-uniform round cross section.

13. The application part of any one of claims 1 or 2, wherein the proximal opening of the working channel includes a clamping device to clamp said fiber optic waveguide.

14. The application part of claim 1 wherein said endoscope is a flexible endoscope.

15. The application part of claim 1 wherein said endoscope is a rigid endoscope.

* * * * *